(12) United States Patent
Minogue et al.

(10) Patent No.: US 7,093,032 B2
(45) Date of Patent: Aug. 15, 2006

(54) SYSTEM AND METHOD FOR MULTI-VENDOR AUTHENTICATION TO REMOTELY ACTIVATE A SOFTWARE-BASED OPTION

(75) Inventors: Michael R. Minogue, Milwaukee, WI (US); Esmeraldo R. V. Davantes, Pewaukee, WI (US); Winnie C. Durbin, Dousman, WI (US); Kun Zhang, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 236 days.

(21) Appl. No.: 10/605,805

(22) Filed: Oct. 28, 2003

(65) Prior Publication Data
US 2005/0091422 A1    Apr. 28, 2005

(51) Int. Cl.
  *G06F 3/00* (2006.01)
  *G06F 13/00* (2006.01)
  *H04L 9/00* (2006.01)

(52) U.S. Cl. ............... 710/8; 710/9; 710/10; 709/243; 713/1; 713/2; 713/182; 700/9

(58) Field of Classification Search ............. 710/8–10; 709/243; 713/1, 2, 182; 700/9
See application file for complete search history.

(56) References Cited

U.S. PATENT DOCUMENTS

| 4,888,798 | A |   | 12/1989 | Earnest |
|---|---|---|---|---|
| 5,014,234 | A |   | 5/1991 | Edwards, Jr. |
| 5,442,541 | A | * | 8/1995 | Hube et al. ................ 700/9 |
| 6,009,153 | A | * | 12/1999 | Houghton et al. ..... 379/102.02 |
| 6,044,471 | A |   | 3/2000 | Colvin |
| 6,272,636 | B1 |   | 8/2001 | Neville et al. |
| 6,301,666 | B1 |   | 10/2001 | Rive |
| 6,360,254 | B1 |   | 3/2002 | Linden et al. |
| 6,490,684 | B1 | * | 12/2002 | Fenstemaker et al. ...... 713/182 |
| 6,664,893 | B1 | * | 12/2003 | Eveland et al. ........ 340/539.12 |
| 6,672,505 | B1 | * | 1/2004 | Steinmetz et al. .......... 235/379 |
| 6,694,384 | B1 | * | 2/2004 | Moeller et al. ................ 710/8 |

* cited by examiner

*Primary Examiner*—Tammara Peyton
(74) *Attorney, Agent, or Firm*—Ziolkowski Patent Solutions Group, SC; Michael A. Della Penna; Carl B. Horton

(57) ABSTRACT

A system and method are provided to remotely activate options resident on a multi-vendor supported device. The technique includes receiving, at a centralized facility, an activation key sent from a first location and configured to activate an option of an in-field device located in a second location, and sending the activation key and a verification script, from the centralized facility, to the in-field device at the second location. The technique also includes receiving, at the centralized facility, a report generated by the verification script and, if the report is satisfactory, installing the activation key in the in-field device to activate the option and, if the report is not satisfactory, aborting activation of the option.

16 Claims, 2 Drawing Sheets

SYSTEM AND METHOD FOR MULTI-VENDOR AUTHENTICATION TO REMOTELY ACTIVATE A SOFTWARE-BASED OPTION

BACKGROUND OF INVENTION

The present invention relates generally to a system to enable software-based options, and more particularly, to remotely verify the status of a multi-vendor supported remote device and, if the remote device is approved, coordinate activation of the desired option though the multiple vendors.

Medical diagnostic devices and supporting systems, such as medical imaging systems, have become increasingly complex in recent years. Examples of such systems include magnetic resonance imaging (MRI) systems, computed tomography (CT) systems, ultrasound and x-ray systems, and positron emission tomography (PET) systems. These systems include many different software-based options, some of which are not used depending on customer needs and costs. To add to the complexity of each particular imaging system, many facilities today incorporate a variety of such devices with components from various vendors all of which may not be configured identically. In larger facilities, the systems may be networked to permit common management and control. Further, such systems may be networked with a picture archiving and communication system (PACS) for storing digitized image data for subsequent retrieval and reconstruction. Additionally, teleradiology systems that involve transmitting digitized image data to remote locations for review and diagnosis by specialized physicians and/or radiologists may be used as well.

Because these medical diagnostic systems are used by different facilities with differing needs, not all of these systems operate identically. That is, although identical software may be installed at the factory, certain options are not desired or licensed by a customer or user and, therefore, are not enabled when delivered. Furthermore, the in-field devices may include components supported by different vendors.

Improvements in computer networks have greatly facilitated the task of offering assistance to remote facilities with medical imaging devices. In particular, rather than having to call a service center and speak with a technician or engineer, or await the arrival of a field engineer, network technologies have facilitated proactive techniques wherein the service center may contact the medical diagnostic devices directly to check the status of the remote devices.

While such advancements in the provision of remote services to medical diagnostic devices have greatly enhanced the level of service and information exchange, they have not been used to remotely verify the status of an in-field device, grant access to and permit use of software options resident on the in-field device.

As such, a customer wishing to activate an option must contact the vendor of the in-field device, schedule the arrival of a field engineer, and then wait for the field engineer to manually evaluate the in-field device and activate the software-based option. That is, if a customer later wants to add inactive options to their devices, a license must be executed and service personnel with appropriate training must physically travel to the location where the devices are present to enable the software. This process can be particularly lengthy and require that the in-field device be removed from service during servicing by the field engineer.

This problem can be compounded when the device is a multi-vendor supported device. That is, due to the complexity of modern medical diagnostic devices, multiple vendors may be required to support a device. For example, it is not uncommon for modern medical diagnostic devices to incorporate components developed and/or supported by a plurality of vendors. As such, when seeking support of such a device, it may be necessary to contact multiple vendors. Therefore, a customer wishing to activate an option may be required to contact multiple vendors, schedule and coordinate the arrival of a field engineer from the various vendors, and then wait for the field engineer to manually evaluate the in-field device and activate the software-based option.

Therefore, it would be desirable to allow automatic activation of a particular option already resident in memory of a device without requiring multiple levels of human interaction to ensure that enabling the particular option is possible and can be implemented without impairing the usability of the device. It would be desirable to have a system to automatically verify the current status of a device requesting access to a particular option and coordinate activation of the option across the multiple support vendors of the device.

BRIEF DESCRIPTION OF INVENTION

The present invention is directed to a system and method to automatically respond to a request for activation of an option resident on a remote device. The system and method are designed to coordinate the activation across multiple support vendors such that the requesting customer is presented with a seamless activation process with a single vendor.

In accordance with one aspect of the invention, an automated method of remotely activating options resident on a multi-vendor supported device is disclosed that includes receiving, at a centralized facility, an activation key sent from a first location and configured to activate an option of an in-field device located in a second location. The method includes sending the activation key and a verification script, from the centralized facility, to the in-field device at the second location. The method then includes receiving, at the centralized facility, a report generated by the verification script and, if the report is satisfactory, installing the activation key in the in-field device to activate the option and, if the report is not satisfactory, aborting activation of the option.

In accordance with one aspect of the invention, a system to respond to a request to remotely enable an option resident on a multi-vendor supported in-field device is disclosed that includes a centralized facility located remotely from an in-field device having an inactive option, and the centralized facility having at least one access computer. The computer is programmed to request an activation key from a remote secondary support provider, select a verification script to check that the in-field device is in condition to activate the inactive option, and send the verification script and the activation key from the centralized facility to the in-field device. The computer is then programmed to permit installation of the activation key in the in-field device to activate the inactive option if the verification script indicates that the in-field device is in condition to activate the inactive option.

In accordance with one aspect of the invention, a system to remotely enable an option resident on an in-field device is disclosed that includes an in-field device located remotely from a centralized facility and a secondary support vendor. The in-field device is programmed to send an access request to the centralized facility to request activation of an inactive option of the in-field device, receive an activation key from the centralized facility that is uniquely configured by the secondary support vendor to activate the option of the in-field device, and receive a verification script from the centralized facility to authenticate a current status of the in-field device. Then in-field device is also programmed to send a report generated by the verification script to the centralized facility indicating the current status of the in-field device and install the activation key to activate the option if the centralized facility indicates the installation is allowable.

Various other features, objects and advantages of the present invention will be made apparent from the following detailed description and the drawings.

BRIEF DESCRIPTION OF DRAWINGS

The drawings illustrate a preferred embodiment as presently contemplated for carrying out the invention.

In the drawings.

DETAILED DESCRIPTION

Figure 1:
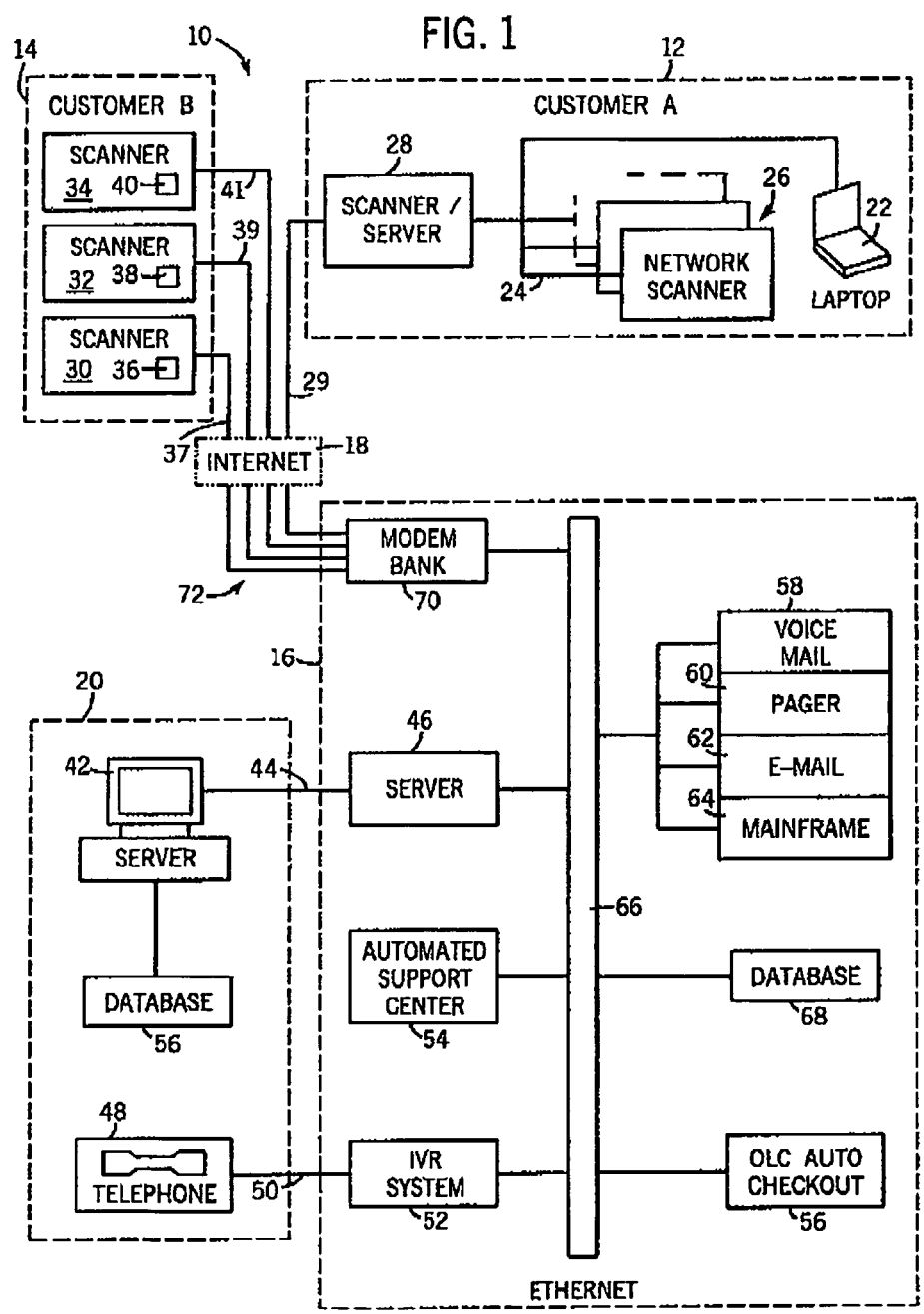
FIG. 1 is a block diagram of a system for which the present invention is implemented therein.

Referring to FIG. 1, an overview block diagram of a medical diagnostic and service networked system 10 is shown which includes a plurality of remote customer stations, such as Customer A in a customer station 12 and Customer B in another customer station 14. It is understood, that the number of customer stations can be limitless, but two specific embodiments are shown with Customer A and Customer B, which will be further explained hereinafter. The customer stations 12, 14 are connected to a first vendor located at a centralized facility 16 through a communications link, such as a network of interconnected server nodes/Internet 18. Although a single centralized facility 16 is shown and described, it is understood that the present invention contemplates the use of multiple centralized facilities, each capable of communication with each customer station. Each customer station has operational software associated therewith which can be configured, serviced, maintained, upgraded, monitored, enabled or disabled by the centralized facility 16.

The centralized facility 16 is connected to a second vendor located at a remote location 20. Although one remotely located secondary vendor 20 is shown and described, it is understood that the present invention contemplates the use of multiple secondary vendors at a plurality of remote locations, each capable of communication with the centralized facility 16.

The various systems of the customer stations 12, 14 are configured to be selectively linked to the centralized facility 16 by, for example, a laptop computer 22 connected to an internal network 24 of Customer A. Such selective linking is desirable to provide upgrades, maintenance, service, and general monitoring of the various systems and equipment at a customer site, which includes accessing data from the systems and transmitting data to the systems, for example.

In general, a customer site may have a number of devices such as a variety of medical diagnostic systems of various modalities and each device may have a variety of enabled and disabled options. As another example, in the present embodiment, the devices may include a number of networked medical image scanners 26 connected to an internal network 24 served by a single scanner 28 having a workstation configured to also act as a server, or configured as a stand-alone server without a medical image scanner associated therewith. Alternately, a customer station, or customer site 14, can include a number of non-networked medical image scanners 30, 32, and 34 each having a computer or work station associated therewith and having an internal modem 36, 38, and 40 to connect the remote customer station to a communications link, such as the Internet 18 through links 37, 39, and 41, respectively, to communicate with the centralized facility 16. Internet 18 is shown in phantom to indicate that an external communications network can include Internet 18, together with communication links 29, 37, 39, and 41, or alternatively, can include direct dial-up links through dedicated lines, an intranet, or public communications systems.

It is understood that each of the network scanners 26 has its own workstation for individual operation and they are linked together by the internal network 24 so that the customer can have a centralized management system for each of the scanners. Further, such a system is provided with communications components allowing it to send and receive data over a communications link 29. Similarly, for the non-networked medical image scanners at remote customer station 14, each of the scanners 30, 32, and 34 have individual communications links 37, 39, and 41. Although FIG. 1 shows each of these links connected through an open network 18, these links can permit data to be transferred to and from the systems over a dedicated network as well.

The embodiment shown in FIG. 1 contemplates a medical facility having such systems as magnetic resonance imaging (MRI) systems, ultrasound systems, x-ray systems, computed tomography (CT) systems, as well as positron emission tomography (PET) systems, or any other type of medical imaging system, however, the present invention is not so limited. Such facilities may also provide services to centralized medical diagnostic management systems, picture archiving and communications systems (PACS), teleradiology systems, etc. Such systems can be either stationary and located in a fixed place and available by a known network address, or be mobile having various network addresses. In the embodiment shown in FIG. 1, each customer station 12, 14 can include any combination of the aforementioned systems, or a customer station may have all of a single type of system. A customer station can also include a single medical image scanner. Mobile diagnostic systems can be configured similarly to that of customer station 12 or customer station 14. Such mobile diagnostic systems can include equipment of various modalities, such as MRI, CT, ultrasound, or x-ray systems and are mobilized in order to service patients at various medical facilities.

A request for access and enablement of software-based options of the present invention can be initiated by authorized personnel, such as an on-line engineer or technician, or customer administrative personnel from, for example, a laptop computer 22 connected to a customer internal network 24, or individually connected to each of the scanners 30, 32, or 34. It is contemplated that the request is an enablement request. That is, a given device is originally purchased having a plurality of options and a customer, due to pricing considerations, may purchase the device with some of the options initially disabled. Therefore, an initial purchase of the hardware of the device includes a wide variety of options and the customer may choose that specific options be disabled to reduce the overall purchase price of the device. Accordingly, after purchase, the customer may make an enablement or activation request to enable any of the options resident on the device at the time of purchase but disabled due to pricing choices. It is further contemplated that the activation request is to enable options added after the initial purchase as part of an update or upgrade but disabled to reduce the price of the upgrade or update.

To fulfill a request for enablement, the centralized facility 16 can communicate with a server 42 of the remotely located secondary vendor 20 via a communications link 44. Specifically, upon receiving an enablement request, a server 46 of the centralized facility 16 contacts the server 42 of the remotely located secondary vendor 20 and communicates a request for an activation key necessary to service the enablement request. The server 42 of the remotely located secondary vendor 20 accesses a database 56 to retrieve stored device information necessary to generate the requested activation key. Once the activation key is generated, the server 42 transfers the key to the centralized facility 16.

A telephone 48 and telephonic connection 50 are provided to facilitate communication between the centralized facility 16 and the secondary vendor 20. The telephone 48 and telephonic connection 50 allows the secondary vendor 20 to communicate with the centralized facility 16 through an interactive voice recognition system (IVR) 52 in the event that generation of the activation key fails. It is understood that the IVR system is not only a voice recognition system, but can also process interactive keypad entry from a touch-tone telephone 48.

Other processor systems of the centralized facility 16 include computers to maintain a voicemail system 58, a pager system 60, an email system 62, and a main frame 64, and more generally, an output report generator and notifier. Each is connectable and can transmit data through a network, such as an Ethernet 66 with one another, and/or with at least one database 68. However, it is understood that the single representation of a database in FIG. 1 is for demonstrative purposes only, and it is assumed that there is a need for multiple databases in such a system. A bank of modems 70 is connected to the Ethernet 66 to relay data from the centralized facility 16 to the remote customer stations 12, 14 through a plurality of modem links 72. Hence, a system to allow automatic remote transfer of data and communications between the centralized facility 16 and a customer site 12, 14 is provided.

As previously discussed, each of the systems and substations described herein and referenced in FIG. 1 may be linked selectively to the centralized facility 16 via a network 18. According to the present invention, any acceptable network may be employed whether public, open, dedicated, private, or so forth. The communications links to the network may be of any acceptable type, including conventional telephone lines, fiber optics, cable modem links, digital subscriber lines, wireless data transfer systems, or the like. Each of the systems is provided with communications interface hardware and software of generally known design, permitting them to establish network links and exchange data with the centralized facility 16. The systems are provided with interactive software so as to configure the systems and exchange data between the customer stations and the centralized facility 16. In some cases, during periods when no data is exchanged between the customer stations and the centralized facility, the network connection can be terminated. In other cases, the network connection is maintained continuously.

The present invention includes a technique for reviewing a remote device for a current status, and if approved for activation, granting access to and remotely permitting use of resident software options in the remote device. As previously indicated, the device, including medical imaging equipment, includes installed software that controls options that can be enabled or disabled automatically. The present invention is directed toward a method and system to automatically and remotely access an in-field device, verify the current status of the in-field device, and coordinate communications between various support vendors to enable options resident on the in-field device.

From a centralized facility 16, and after appropriate authentication of the user and validation of the system identification and customer's status, the centralized facility 16 requests an electronic enabler in the form of an activation key from the secondary vendor 20. The secondary vendor 20 generates the activation key and returns it to the centralized facility 16, whereby the centralized facility 16 electronically transmits the activation key to a device via the communication links 29, 37, 39, 41, and/or 72. Preferably, the communication is over a private communication link, but other public communications systems can work equally well, such as direct dial-up internet, or wireless communications. As previously set forth, it is understood that the external communications links include a closed intranet system, an open public communications system, or a combination thereof.

Figure 2:
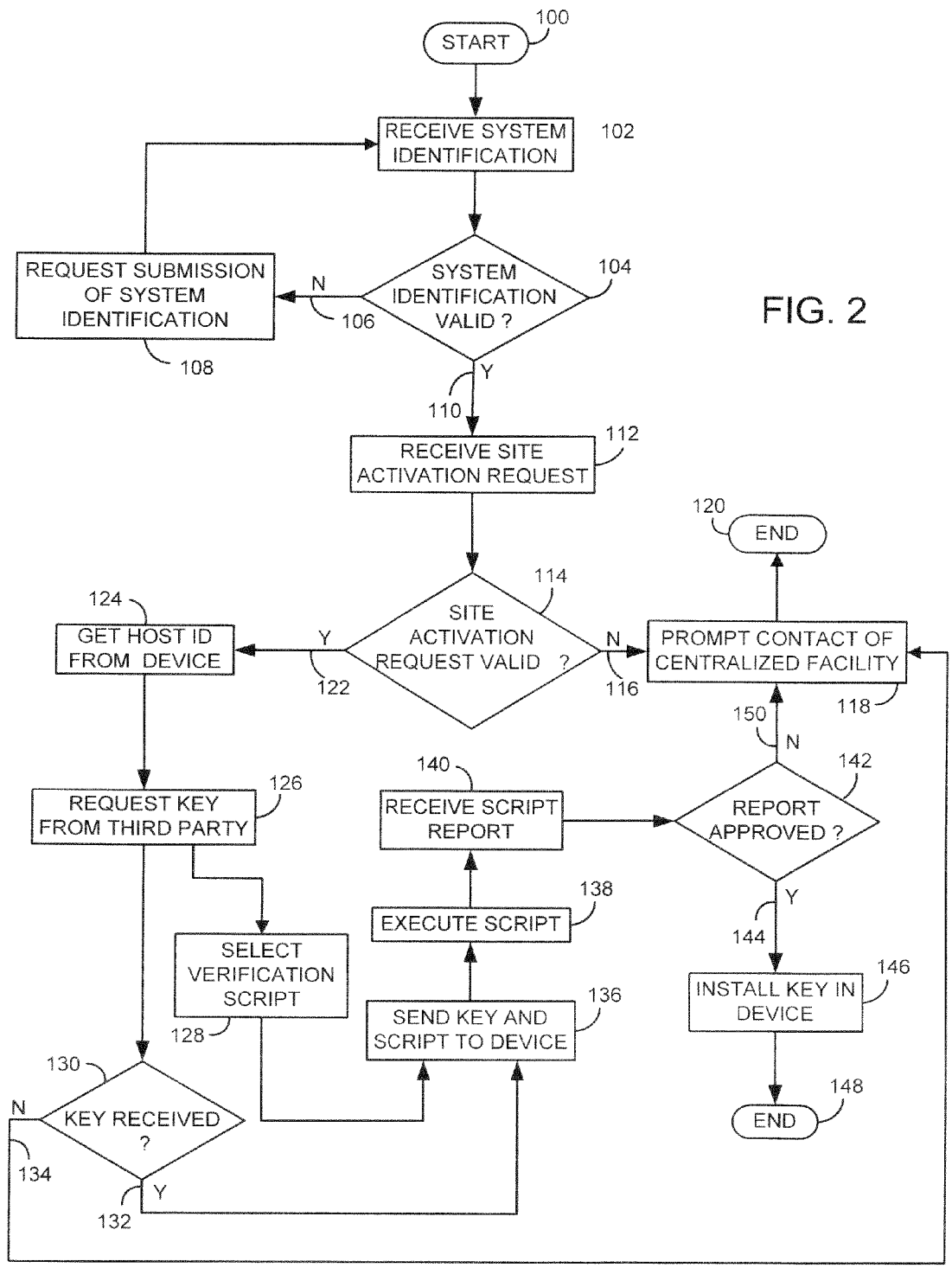
FIG. 2 is a flow chart showing a process of the present invention and implemented in the system of FIG. 1.

Referring to FIG. 2, the technique is initiated 100 when a system identification including customer identification is sent from a remote customer station and received at the centralized facility 102. It is contemplated that the system identification constitutes the initiation of an enablement request. That is, the requesting device may have been originally purchased having a plurality of options and, due to pricing considerations, the device was purchased with some of the options initially disabled. Therefore, the initial purchase of the hardware of the device included a wide variety of options and the customer may have chosen that specific options be disabled to reduce the overall purchase price of the device. Accordingly, after purchase, the customer may make an enablement or activation request to enable any of the options resident on the device at the time of purchase but disabled due to pricing choices. It is further contemplated that the activation request may be to enable options added after the initial purchase as part of an update or upgrade but disabled to reduce the price of the upgrade or update.

After receiving the system identification, the centralized facility then validates the system identification at 104. Validation is determined according to the customer identification and/or a passphrase. The system identification constitutes a unique identification that enables the centralized facility to readily identify the customer making the request and the customer's in-field devices. If the customer identification is not valid 106, a prompt for entry of a valid customer identification is requested 108. After the system identification is validated 104, 110, a request for a particular software option that is desired to be activated is sent from the in-field device requesting activation and is received at the centralized facility 112. The centralized facility then validates the activation request at 114. Specifically, the centralized facility makes an initial review of the activation request by comparing the system identification to the activation request. The centralized facility determines whether the system is generally capable of the activation requested. For example, the centralized facility determines whether the requested activation has previously been made and fulfilled, and therefore, the option is already enabled.

If the activation request 112 is determined to be invalid 116, e.g., does not register the requesting in-field device as including or supporting the software-based option requested or the requested option is already active, a message is returned to the in-field device to prompt manual contact with the centralized facility 118 and the activation is aborted 120.

However, if the activation request is determined to be valid 122, the in-field device then sends a unique host identifier to the centralized facility 124. The unique host identifier indicates, to the centralized facility, the specific in-field device where activation is requested. Upon receipt of the host ID 124, the centralized facility passes the host ID to a remotely located secondary vendor in the form a request for an activation key 126.

Based on the host ID, the remotely located secondary vendor generates an activation key configured to activate the desired option upon installation in the in-field device. Concurrently, the centralized facility selects a verification script 128 appropriate to determine a current status of the in-field device 126. The centralized facility waits for a response from the remotely located secondary vendor 130. It is contemplated that a response may be a receipt of the requested activation key 132 or an error communication indicating an activation key cannot be generated 134. If an error report is communicated, the centralized facility reviews the report to determine the error and returns a prompt for manual contact with the centralized facility 118, thereby aborting activation 120.

On the other hand, once the activation key has been received 132 and the verification script selected 128, the centralized facility sends the key and script to the in-field device 136. It is contemplated that script and key may be sent to the in-field device in a single transmission or through multiple transmissions. Furthermore, if a single transmission is made, the key and script may be bundled together to create a single package that is sent to the in-field device. It is further considered that the single package may be compressed and/or encrypted to expedite and secure transmission.

When the in-field device receives the key and script, the device unbundles the package, if necessary, and executes the verification script 138. The verification script is configured to automatically determine a current status of the in-field device requesting option activation. Specifically, the verification script gathers a plurality of current settings of the in-field device and generates a report. For example, the verification script may determine which options are currently active on the in-field device, which options are supported by the in-field device, any dependencies of options supported by the in-field device, as well as other similar settings. The report contains information regarding the enableability of the in-field device with respect to the requested option. That is, the information included in the report pertains to the current setting of the in-field device and whether, under those settings, the in-field device is in condition to have the requested option enabled, i.e. the enableability of the in-field device. The information is then used by the verification script to generate a report that is sent by the in-field device and received by the centralized facility 140. The centralized facility then evaluates the report 142 to determine the enableability of the in-field device with respect to the requested option.

If the report indicates the device is enableable, the report is approved 144 and the centralized facility permits installation of the activation key in the in-field device 146. Specifically, the centralized facility sends an approval to the in-field device whereby the in-field device installs the activation key enabling the option 146 and the activation of the option is complete 148. However, the centralized facility may monitor the use of the option. As such, the activation key may contain a preset expiration time, whereby the centralized facility may warn the customer of an impending expiration. Should the customer elect to reactivate the option, the steps described above are repeated and the option is reactivated.

However, if the report indicates that the desired option cannot readily be activated, the centralized facility does not approve the report 150. Accordingly, a message is returned to the in-field device to prompt manual contact with the centralized facility 118 and the activation is aborted 120.

Accordingly, the present invention includes a method to remotely activate an option resident in the memory of an in-field device requiring multiple vendor approval without requiring the customer to contact each vendor or compromising the functionality of the in-field device.

The present invention includes a method to remotely activate options resident on a multi-vendor supported device. The method includes receiving, at a centralized facility, an activation key sent from a first location and configured to activate an option of an in-field device located in a second location and sending the activation key and a verification script, from the centralized facility, to the in-field device at the second location. The method then includes receiving, at the centralized facility, a report generated by the verification script and, if the report is satisfactory, installing the activation key in the in-field device to activate the option and, if the report is not satisfactory, aborting activation of the option.

The present invention includes a system to respond to a request to remotely enable an option resident on a multi-vendor supported in-field device. The system includes a centralized facility located remotely from an in-field device having an inactive option, and the centralized facility having at least one access computer. The computer is programmed to request an activation key from a remote secondary support provider, select a verification script to check that the in-field device is in condition to activate the inactive option, and send the verification script and the activation key from the centralized facility to the in-field device. The computer is then programmed to permit installation of the activation key in the in-field device to activate the inactive option if the verification script indicates that the in-field device is in condition to activate the inactive option.

The present invention includes a system to remotely enable an option resident on an in-field device. The system includes an in-field device located remotely from a centralized facility and a secondary support vendor. The in-field device is programmed to send an access request to the centralized facility to request activation of an inactive option of the in-field device, receive an activation key from the centralized facility that is uniquely configured by the secondary support vendor to activate the option of the in-field device, and receive a verification script from the centralized facility to authenticate a current status of the in-field device. The in-field device is also programmed to send a report generated by the verification script to the centralized facility indicating the current status of the in-field device and install the activation key to activate the option if the centralized facility indicates the installation is allowable.

The present invention has been described in terms of the preferred embodiment, and it is recognized that equivalents, alternatives, and modifications, aside from those expressly stated, are possible and within the scope of the appending claims.

What is claimed is:

1. An automated method of remotely activating options resident on a multi-vendor supported device comprising the steps of:
   receiving, at a centralized facility, an activation key sent from a first location and configured to activate an option of an in-field device located in a second location;
   sending the activation key and a verification script, from the centralized facility, to the in-field device at the second location;
   receiving, at the centralized facility, a report generated by the verification script; and
   if the report is satisfactory, installing the activation key in the in-field device to activate the option and if the report is not satisfactory, aborting activation of the option.

2. The method of claim 1 wherein the in-field device located in the second location does not communicate with the first location.

3. The method of claim 1 further comprising the step of bundling and compressing the activation key and the verification script together for transmission to the in-field device located in the second location.

4. The method of claim 1 wherein report includes at least one of:
   options currently active;
   options supported by the in-field device; and
   dependencies of options supported by the in-field device.

5. The method of claim 4 further comprising the step of determining if the report is unsatisfactory by determining from the report whether the option to be activated is one of currently active, not supported by the in-field device, and requires dependent activations.

6. The method of claim 5 further comprising the step of automatically sending a message from the centralized facility to the second location prompting contact with a centralized facility if the report is unsatisfactory.

7. The method of claim 1 wherein the activation key is unique to the in-field device.

8. The method of claim 1 further comprising the step of receiving an access request from the in-field device at a centralized facility and requesting the activation key from the first location in response thereto.

9. The method of claim 8 further comprising suspending the access request and repeating the request for the activation key from the first location until an activation key is received from the first location.

10. The method of claim 1 wherein the in-field device is configured for medical imaging.

11. A system to remotely enable an option resident on an in-field device, the system comprising:
    an in-field device located remotely from a centralized facility and a secondary support vendor and programmed to:
    send an access request to the centralized facility to request activation of an inactive option of the in-field device;
    receive an activation key from the centralized facility that is uniquely configured by the secondary support vendor to activate the option of the in-field device;
    receive a verification script from the centralized facility to authenticate a current status of the in-field device;
    send a report generated by the verification script to the centralized facility indicating the current status of the in-field device; and
    install the activation key to activate the option if the centralized facility indicates the installation is allowable.

12. The system of claim 11 wherein the access request includes a host ID that is unique to the in-field device and that is relayed from the centralized facility to the secondary support vendor to generate the activation key.

13. The system of claim 11 wherein the in-field device, secondary support vendor, and centralized facility are remotely located from one another.

14. The system of claim 11 wherein the current status of the in-field device is unsatisfactory if the report indicates that at least one of: the option is currently active, the in-field device does not support the option, and absent dependencies preclude activation of the option.

15. The system of claim 11 wherein the activation key and the verification script are received by the in-field device as a compressed bundle.

16. The system of claim 11 wherein the in-field device includes a medical imaging device.

* * * * *